(12) United States Patent
Berlin

(10) Patent No.: US 7,863,287 B2
(45) Date of Patent: *Jan. 4, 2011

(54) COMPOSITIONS OF NON-STEROIDAL ANTI-INFLAMMATORY DRUGS, DECONGESTANTS AND ANTI-HISTAMINES

(75) Inventor: Roger G. Berlin, Mendham, NJ (US)

(73) Assignee: Wyeth LLC, Madison, NJ (US)

( * ) Notice: Subject to any disclaimer, the term of this patent is extended or adjusted under 35 U.S.C. 154(b) by 1169 days.

This patent is subject to a terminal disclaimer.

(21) Appl. No.: 10/740,386

(22) Filed: Dec. 17, 2003

(65) Prior Publication Data

US 2004/0186184 A1  Sep. 23, 2004

Related U.S. Application Data

(60) Provisional application No. 60/434,342, filed on Dec. 18, 2002.

(51) Int. Cl.
*A61K 31/435* (2006.01)
*A61K 31/015* (2006.01)

(52) U.S. Cl. ........................ 514/277; 514/764
(58) Field of Classification Search ............... 514/277, 514/764

See application file for complete search history.

(56) References Cited

U.S. PATENT DOCUMENTS

| | | | |
|---|---|---|---|
| 4,522,826 A | 6/1985 | Sunshine et al. | |
| 4,552,899 A | 11/1985 | Sunshine et al. | |
| 4,585,783 A | 4/1986 | Sunshine et al. | |
| 4,683,243 A | 7/1987 | Sunshine et al. | |
| 4,738,966 A | 4/1988 | Sunshine et al. | |
| 4,749,697 A | 6/1988 | Sunshine et al. | |
| 4,749,711 A | 6/1988 | Sunshine et al. | |
| 4,749,720 A | 6/1988 | Sunshine et al. | |
| 4,749,721 A | 6/1988 | Sunshine et al. | |
| 4,749,722 A | 6/1988 | Sunshine et al. | |
| 4,749,723 A | 6/1988 | Sunshine et al. | |
| 4,755,532 A | 7/1988 | Sunshine et al. | |
| 4,783,465 A | 11/1988 | Sunshine et al. | |
| 4,829,064 A | 5/1989 | Sunshine et al. | |
| 4,839,354 A | 6/1989 | Sunshine et al. | |
| 4,840,962 A | 6/1989 | Sunshine et al. | |
| 4,871,733 A | 10/1989 | Sunshine et al. | |
| 4,906,625 A | 3/1990 | Sunshine et al. | |
| 4,920,149 A | 4/1990 | Sunshine et al. | |
| 4,952,402 A | 8/1990 | Sparks et al. | |
| 4,975,426 A | 12/1990 | Sunshine et al. | |
| 4,985,459 A | 1/1991 | Sunshine et al. | |
| 4,990,535 A | 2/1991 | Cho et al. | |
| 5,025,019 A * | 6/1991 | Sunshine et al. | 514/277 |
| 5,133,974 A | 7/1992 | Paradissis et al. | |
| 5,196,436 A | 3/1993 | Smith | |
| 5,288,479 A | 2/1994 | Gorman et al. | |
| 5,374,659 A | 12/1994 | Gowan, Jr. | |
| 5,466,865 A | 11/1995 | Geyer et al. | |
| 5,492,689 A | 2/1996 | Gwaltney | |
| 5,560,913 A | 10/1996 | Kupper | |
| 5,622,723 A | 4/1997 | Bettman et al. | |
| 5,681,577 A | 10/1997 | Lech et al. | |
| 5,869,479 A | 2/1999 | Kreutner | |
| 5,895,663 A | 4/1999 | Irwin et al. | |
| 6,090,411 A | 7/2000 | Pillay et al. | |
| 6,210,710 B1 | 4/2001 | Skinner | |
| 6,270,796 B1 | 8/2001 | Weinstein | |
| 6,294,195 B1 | 9/2001 | Oshlack et al. | |
| 6,337,091 B1 | 1/2002 | Kim et al. | |
| 6,384,054 B1 | 5/2002 | Woosley | |
| 6,517,868 B2 | 2/2003 | Fassihi et al. | |
| 6,709,676 B2 | 3/2004 | Cho | |

FOREIGN PATENT DOCUMENTS

| | | |
|---|---|---|
| AU | 738274 B2 | 9/2001 |
| CA | 2084028 | 5/1993 |
| EP | 0674517 | 10/1995 |
| JP | 2002316927 A | 10/2002 |

(Continued)

OTHER PUBLICATIONS

Winter, et al., *The Therapeutic Effectiveness of Ibuprofen on the Symptoms of Naturally Acquired Acquired Common Colds*, American Journal of Rhinology, 15 (2001), 239-242.

(Continued)

*Primary Examiner*—Sreeni Padmanabhan
*Assistant Examiner*—Renee Claytor
(74) *Attorney, Agent, or Firm*—Jeffrey M. Gold

(57) ABSTRACT

The present invention is directed to a pharmaceutical composition and method for the treatment of rhinitis and cold-like symptoms which includes a non-steroidal anti-inflammatory drug (NSAID), a decongestant, and an antihistamine. It has been found that an NSAID enhances the activity of a decongestant and an anti-histamine, thus permitting a reduction in either or both in administration of separate dosage forms. The same enhancement can also occur with an anti-tussitive. Thus, the effective amount of the decongestant or the antihistamine or both is less than about 75% of an amount present in an approved dose of the decongestant or the antihistamine, or both, relative to an amount of the NSAID corresponding to about 100% of the amount present in a normal strength dosage form of the NSAID.

9 Claims, No Drawings

FOREIGN PATENT DOCUMENTS

| WO | 85/04589 | | 10/1985 |
|---|---|---|---|
| WO | 0448895 | A1 | 10/1991 |
| WO | 92/04021 | A1 | 3/1992 |
| WO | 92/04022 | A1 | 3/1992 |
| WO | 92/17171 | A1 | 10/1992 |
| WO | 94/14449 | A1 | 7/1994 |
| WO | 94/14476 | A1 | 7/1994 |
| WO | 95/07079 | A1 | 3/1995 |
| WO | 95/07103 | | 3/1995 |
| WO | 95/11677 | | 5/1995 |
| WO | 97/04808 | | 2/1997 |
| WO | 97/04808 | | 3/1997 |
| WO | 98/06436 | A2 | 2/1998 |
| WO | 99/15173 | A1 | 4/1999 |
| WO | 01/21168 | A1 | 3/2001 |
| WO | 03/089007 | | 10/2003 |
| WO | 2005/063219 | A2 | 7/2005 |
| WO | 02/96406 | A1 | 12/2005 |

OTHER PUBLICATIONS

Sperber, et al., *Evaluation of an Alpha Agonist Alone and in Combination with a Nonsteroidal Antiinflammatory Agent in the Treatment of Experimental Rhinovirus Colds*, Bull. N.Y. Acad. Med., 65 (1989), 145-160.

Chua et al: "Cardiovascular effects of a chlorpheniramine/paracetamol combination in hypertensive patients who were sensitive to the pressor effect of pseudoephedrine" Br J Clin Pharmacol. Mar. 1991; 31(3):360-2.

Sperber et al: "Evaluation of an alpha antagonist alone and in combination with a nonsteroidal antiinflammatory agent in the treatment of experimental rhinovirus colds" BII NY Acad. Med. Jan. 1989 65(1): 145-60.

Weidinger et al.: "Oral phenylephrine: An ineffective replacement for pseudoephedrine?" The Journal of Allergy and Clinical Immunology. 2006. vol. 118 No. 1. pp. 279-280.

Children's Dimetapp® product information (http://www.dimetapp.com/coldlbl,_chew.asp).

Sudafed PE® product information (http://www.sudafed.com/products/sudafed_pe.html).

Children's Sudafed® product information (http://www.sudafed.com/products/childrens_chewables.htm).

Sudafed® product information ( http://www.sudafed.com/products/sudafed.html).

\* cited by examiner

COMPOSITIONS OF NON-STEROIDAL ANTI-INFLAMMATORY DRUGS, DECONGESTANTS AND ANTI-HISTAMINES

This application claims the benefit of U.S. provisional application No. 60/434,342, filed Dec. 18, 2002, which is incorporated by reference herein in its entirety.

FIELD OF THE INVENTION

The present invention relates to improved dosage forms of pharmaceuticals for treating rhinitis associated with allergies and colds.

BACKGROUND OF THE INVENTION

Decongestants and Antihistamines

Rhinitis refers to an inflammatory disorder of the nasal passages. The symptoms of rhinitis typically consist of sneezing, rhinorrhea, nasal congestion, and increased nasal secretions. Untreated rhinitis may lead to other disorders including infection of the sinuses, ears and lower respiratory tract.

Two types of oral medication are commonly used to treat rhinitis: decongestants and antihistamines. Decongestants and antihistamines differ in mechanism of action, therapeutic effects, and side effects. It is common practice to combine the use of these two to bring about more complete symptom relief of rhinitis than is possible with either entity alone.

Decongestants commonly used to treat rhinitis include the sympatomimetic agents pseudoephedrine and phenylephrine. These agents act to constrict vessels in the nasal mucus membranes and thereby decrease tissue swelling and nasal congestion. Decongestants are found to be better than antihistamines for restoring the patency of congested nasal airways. Nasal decongestants are stimulatory. Decongestants, however may produce nervousness, restlessness and insomnia, especially if taken at night Histamine is a mediator released from cells which line the walls of the nasal mucous membranes (mast cells). When released, histamine is known to bind to local receptors and thereby cause sneezing, nasal itching, swelling of the nasal membranes, and increased nasal secretions. Antihistamines relieve these effects, albeit by a different mechanism than decongestants. Antihistamines block the binding of histamine to histamine receptors in the nasal membranes. Side effects of antihistamines include impairment of mental acuity and sedation.

Combinations of decongestants and antihistamines employ two mechanistic approaches, and have been shown to offer more complete relief of rhinitis symptoms than therapy with either component alone. Currently, many cold and allergy relief products contain both. Incorporation of decongestant and sedating antihistamine into a single dosage unit balances stimulation and sedation of the components. However, some individuals vary in there sensitivity to either the decongestant or the antihistamine. Consequently, some individuals experience irritability and/or sedation with these combinations.

Examples of commercial formulations containing decongestant and sedating antihistamine include:

1. CHLOR-TRIMETON.™. 4 hour Allergy/Decongestant which contains 4 mg of chlorpheniramine (sedating antihistamine) and 60 mg pseudoephedrine sulfate (stimulating decongestant), and which is recommended to be taken every 4 to 6 hours (½ this dosage for children 6 to under 12);
2. CHLOR-TRIMETON.™. 12 hour Allergy/Decongestant which contains 8 mg of chlorpheniramine (sedating antihistamine) and 120 mg pseudoephedrine sulfate (stimulating decongestant), and which is recommended to be taken every 12 hours (adults and children over 12 years of age only);
3. BROMFED™. Tablets which contains 4 mg of brompheniramine (sedating antihistamine) and 60 mg pseudoephedrine sulfate (stimulating decongestant), and which is recommended to be taken every 4 to 6 hours (½ this dosage for children 6 to under 12);
4. BROMFED.™. Capsules which contains 12 mg of brompheniramine (sedating antihistamine) and 120 mg pseudoephedrine sulfate (stimulating decongestant), and which is recommended to be taken every 12 hours (adults and children over 12 years of age only);
5. BENADRYL™. Allergy Decongestant Tablets which contains 25 mg of diphenhydramine hydrochloride (sedating antihistamine) and 60 mg pseudoephedrine sulfate (stimulating decongestant), and which is recommended to be taken by adults and children over 12 years of age every 4 to 6 hours, not to exceed 4 tablets in 24 hours; and
6. TAVIST-D™. Tablets which contains 1.34 mg clemastine fumarate (sedating antihistamine) and 75 mg phenylpropanolamine hydrochloride (stimulating decongestant), and which is recommended to be taken every 12 hours (adults and children over 12 years of age only).

Formulations have been commercialized that incorporate both a decongestant and a non-sedating antihistamine into a single dosage unit. While such formulations offer the advantage in being non-sedating, their efficacy does not approach that offered by sedating antihistamines, especially for rhinitis due to colds.

Non-steroidal Anti-inflammatory Drugs

Non-steroidal anti-inflammatory drugs (NSAIDS) are ideally suited for use in cold formulations for their analgesic, anti-inflammatory, and antipyretic activity and low incidence of untoward side effects. Exemplary cold formulations containing non-steroidal anti-inflammatory agents include Advil Cold and Sinus™, Motrin Cold and Flu™, Motrin IB Sinus™ and Dristan Sinu™, each containing 200 mg ibuprofen and 30 mg pseudoephedrine.

U.S. Pat. No. 5,025,019 teaches pharmaceutical compositions and methods of using a composition containing a non-steroidal anti-inflammatory drug in combination with at least one other active component selected from an antihistamine, decongestant, cough suppressant or expectorant.

While these combination products provide effective symptom treatment of rhinitis due to cold and allergy, they do not alleviate the side effects of decongestants and antihistamines in sensitive individuals. Thus there remains a need in the art to treat symptoms of rhinitis but reduce the side effects from the treatment.

SUMMARY OF THE INVENTION

The present invention is directed to a pharmaceutical composition which includes an effective amount of each of a non-steroidal anti-inflammatory drug (NSAID), a decongestant, and an antihistamine, wherein the effective amount of the decongestant or the antihistamine or both is less than about 75% of an amount present in an approved dose of the decongestant or the antihistamine, or both, relative to an amount of the NSAID corresponding to about 100% of the amount present in a normal strength dosage form of the NSAID.

An embodiment of the invention is a pharmaceutical composition containing from about 10 to about 60 mg pseudoephedrine hydrochloride per dosage unit, from about 1 to about 4 mg chlorpheniramine per dosage unit, and from about 200 to about 400 mg ibuprofen per dosage unit.

The present invention is further directed to a method of relieving symptoms of rhinitis in a mammal. This method comprises administering an antihistaminic effective amount of an antihistamine, a decongestive effective amount of a decongestant, and an anti-inflammatory effective amount of a non-steroidal anti-inflammatory agent, wherein the effective amount of the decongestant or the antihistamine or both is less than about 75% of an amount present in an approved dose of the decongestant or the antihistamine, or both, relative to an amount of the NSAID corresponding to about 100% of the amount present in a normal strength dosage form of the NSAID. Preferably in accordance with this method the antihistamine, the decongestant and the non-steroidal anti-inflammatory agent are present in a single dosage form. However, they can also be provided in separate dosage forms for administration together, or as separate dosage forms with instructions of how to achieve the effective dosages of the invention.

In addition to the three components, an anti-tussive agent can also be delivered in accordance with this invention.

DETAILED DESCRIPTION OF THE INVENTION

It has been discovered that the addition of a non-steroidal anti-inflammatory agent to a composition containing an antihistamine and/or a decongestant enchances the efficacy of the antihistamine and decongestant, thus permitting a reduction in the total dose of either or both. In particular, the amount of antihistamine and/or the decongestant can be less or equal to about 75% of an amount present in an approved dose of the decongestant or the antihistamine relative to an amount of the NSAID corresponding to about 100% of the amount present in a normal strength dosage form of the NSAID. This combination of a 100% dose of an NSAID with a reduced dose of an antihistamine or a decongestant or both results in an enhanced effect of the decongestant and/or antihistamine. This novel combination of a non-steroidal anti-inflammatory agent with reduced levels of antihistamine and/or decongestant provides the same or greater symptomatic relief of rhinitis, including allergy, cold, cold-like, and flu symptoms, as conventional products containing the higher amounts of antihistamine and decongestants. This discovery is particularly advantageous because lowering the amounts of antihistamine and decongestant is likely to lower the unwanted side effects of each of these ingredients, such as the stimulatory effect of decongestants and drowsiness associated with antihistamines.

As used herein, the term "rhinitis" refers to inflammation of the nasal mucous membranes, which could result from a cold, flu, or allergies. Rhinitis may be characterized by one or more cold-like symptoms.

Cold-like symptoms as used herein refers to coryzea, nasal congestion, upper respiratory infections, allergic rhinitis, otitis, sinusitis, and the like. Runny nose and nasal congestion can also be cold symptoms.

The terms "effective amount" or "therapeutically effective amount" of an active agent as provided herein is defined as an amount of the agent at least sufficient to provide the desired therapeutic effect. As noted above, the present invention is based on the discovery that the effective dose of a decongestant and/or antihistamine can be reduced if administered with a normal dose of a NSAID. The exact amount required will vary from subject to subject, depending on age, general condition of the subject, the severity of the condition being treated, and the particular active agent administered, and the like.

The term "normal approved dose" of an active agent as provided herein is defined as an amount of the agent that has been approved as safe and effective by the United States Food and Drug Administration for administration in humans in a particular dosage form. An approved dose is thus a dose found in a pharmaceutical product, an amount of active agent per unit dosage form. In the present invention, reference to a ratio of approved doses means doses approved for the same patient population (e.g., adult to adult or pediatric to pediatric), and approved for the same dosage form (e.g., elixir, tablet, capsule, caplet, controlled release, etc.).

In the practice of the invention, one of ordinary skill in the art can take an approved dosage form of any over-the-counter (OTC) or prescription decongestant and/or antihistamine, reduce it by, e.g., 25% to 50% or more, and co-administer it with an approved amount (dose) of a NSAID to achieve effective relief of rhinitis with reduced side effects. In one embodiment, the present invention contemplates the use of less than or equal to about 75% and more that 1% of an amount present in an approved dose of one or more of the decongestant, antitussitive or the antihistamine, relative to an amount of the NSAID corresponding to about 100% of the amount present in a normal strength dosage form of the NSAID. An alternate range is from about 10% to about 65%. Another range is from about 30% to about 55%. Ranges from about 35% to about 50% are also possible.

While the present invention contemplates compositions comprising all three components (i.e., decongestant, antihistamine and NSAID), with the decongestant or antihistamine, or both, present in a lower amount relative to conventional OTC decongestant and/or antihistamine products on the market, one can readily achieve the present invention by reducing the dose of the conventional antihistamine and/or decongestant products on the market when they are administered with a product containing a normal dose of a NSAID. Such reductions can be achieved by cutting an adult dose in half, e.g., administering half the amount of elixir or cutting a tablet in half, or by using a reduced dosage form, such as a decongestant and/or antihistamine product formulated for children in combination with an adult formulation of an NSAID at the approved dose.

Antihistamines

The term "antihistamine", used in connection with treating nasal symptoms associated with allergy or cold, generally refers to histamine $H_1$ receptor antagonists. Numerous chemical substances are known to have histamine $H_1$ receptor antagonist activity. Many useful compounds can be classified as ethanolamines, ethylenediamines, alkylamines, phenothiazines or piperidines. Representative $H_1$ receptor antagonists, include, without limitation: astemizole, azatadine, azelastine, acrivastine, brompheniramine, chlorpheniramine, clemastine, cyclizine, carebastine, cyproheptadine, carbinoxamine, descarboethoxyloratadine (also known as SCH-34117), desloratadine doxylamine, dimethindene, ebastine, epinastine, efletirizine, fexofenadine, hydroxyzine, ketotifen, loratadine, levocabastine, mizolastine, mequitazine, mianserin, noberastine, meclizine, norastemizole, picumast, pyrilamine, promethazine, terfenadine, tripelennamine, temelastine, trimeprazine and triprolidine. Other compounds can readily be evaluated to determine activity at $H_1$ receptors by known methods, including specific blockade of the contractile response to histamine of isolated guinea pig ileum.

Of the foregoing histamine $H_1$ receptor antagonists, chlorpheniramine is specifically exemplified herein. The usual adult dosage of chlorpheniramine is 4 mg orally every 4-6 hours as needed, up to a maximum of 24 mg per day. The usual pediatric dosage of chlorpheniramine is 2 mg orally every 4-6 hours, up to a maximum of 12 mg per day. The preferred salt is chlorpheniramine maleate. In accordance with the present invention, the usual adult dosage is thus reduced to 3 mg, or further to 2 mg, orally every 4-6 hours as needed, up to a maximum of 12-18 mg per day. Similarly, in an embodiment of the invention, the pediatric dosage is 1.5 mg, or 1 mg, orally every 4-6 hours, up to a maximum of 6-9 mg per day. In a further embodiment, the invention permits combining a pediatric dosage of chlorpheniramine with an adult dosage of an NSAID, such as ibuprofen.

Decongestants

The decongestants for use in the pharmaceutical compositions and methods of use of the present invention include, but are not limited to, pseudoephedrine, phenylephrine, and phenylpropanolamine. One of skill in the art would know of many other appropriate decongestants and their approved dosages.

The exemplified decongestant is pseudoephedrine. The usual adult dose of pseudoephedrine is 60 mg every 4-6 hours, up to a maximum of 240 mg per day. The usual pediatric dose of pseudoephedrine is 15 mg every 6 hours, up to a maximum of 60 mg per day for ages 2-5 and 30 mg every 6 hours, up to a maximum of 120 mg per day for ages 6-12. Thus, in specific embodiments of the practice of the present invention, the adult dose can be reduced to 45 or 30 mg every 4-6 hours, with a maximum of 120 to 180 mg per day, and the pediatric dose can be reduced to about 11 or 7.5 mg every 6 hours, up to a maximum of 30-45 mg per day. From the foregoing it is apparent that the invention contemplates administering a double pediatric dose with a normal adult dose of an NSAID to an adult.

NSAIDs

The non-steroidal anti-inflammatory drugs (NSAID's) for use in the pharmaceutical compositions and methods of use of the present invention may be selected from any of the following categories:

(1) The propionic acid derivatives;
(2) the acetic acid derivatives;
(3) The fenamic acid derivatives
(4) The biphenylcarboxylic acid derivatives;
(5) The oxicams, and
(6) Cox-2 inhibitors Accordingly, the term "NSAID" as used herein is intended to mean any non-steroidal anti-inflammatory compound, including the pharmaceutically acceptable non-toxic salts thereof, falling within one of the six structural categories above.

The specific compounds falling within the foregoing definition of the non-steroidal anti-inflammatory drugs for use in the present invention are well known to those skilled in the art and reference may be found in various literature reference sources for their chemical structures, pharmacological activities, side effects, normal dosage ranges, etc. See, for example, Physician's Desk Reference, and The Merek Index.

Of the propionic acid derivatives for use herein, ibuprofen, naxproxen, flurbiprofen, fenoprofen, ketoprofen, suprofen, fenbufen, and fluprofen may be mentioned as exemplified compounds. Of the acetic acid derivatives, exemplary compounds include tolmetin sodium, zomepirac, sulindac and indomethacin. Of the fenamic acid derivatives, exemplary compounds include mefenamic acid and meclofenamate sodium. Exemplary biphenylcarboxlic acid derivatives for use in the present invention include diflunisal and flufenisal. Exemplary oxicams include piroxicam, sudoxicam and isoxicam. Exemplary Cox-2 inhibitors include celecoxib, rofecoxib, meloxicam, and nimesulide. Of the foregoing non-steroidal anti-inflammatory drugs, in the practice of the exemplified embodiments of the present invention, ibuprofen is exemplified.

With respect to the dosage amount of the non-steroidal anti-inflammatory drugs in the compositions of the invention, although the specific dose will vary depending upon the age and weight of the patient, the severity of the symptoms, the incidence of side effects and the like, for humans, typical effective analgesic amounts of NSAID's are about 100-500 mg diflunisal, about 25-100 mg zomepirac sodium, about 50-400 mg ibuprofen, more preferably 100-200 mg ibuprofen, about 125-500 mg naproxen, about 25-100 mg flurbiprofen, about 50-199 mg fenoprogen, about 10-20 mg piroxicam, about 125-250 mg mefanaic acid, about 100-400 mg fenbufen or about 25-50 mg ketoprofen; however, greater or lesser amounts may be employed if desired or necessary.

Anti-Tussitives

Anti-tussitives act on the brain to suppress the cough reflex. Such cough suppressants are used to relieve dry persistent coughs. The most commonly used drugs are dextromethorphan (an NMDA receptor antagonist), codeine and pholcodine (which are opioids. However, one skilled in the art would understand that there are many other well known and common anti-tussitives that may be used. The present invention is optionally direct to the use of anti-tussitves. The anti-tussitive may be used in amounts of less than or equal to 75% of the approved approved dosage.

Pharmaceutical Compositions

Compositions of the invention are formulated in a single dosage form, and these may be solid (such as tablets, capsules, sachets, trochets and the like), liquid (such as solutions or suspensions) or inhalation aerosols or patches. While the solid compounds will typically be administered orally, the liquids may be administered orally or by injection. Other dosage forms, such as suppositories, are also useful.

Exlempary compositions of the present invention are directed to solid dosage forms such as bulk powders, tablets, caplets, pellets, capsules, sachets, granules, and any other dosage form suitable for oral administration. For purposes of this specification and the accompanying claims, the term "tablet" refers equally to a tablet, a caplet or any other solid dosage form which is suitable for oral administration.

Binders are agents used to impart cohesive qualities to the powdered material. Binders impart cohesiveness to the tablet formulation which insures the tablet remaining intact after compression, as well as improving the free-flowing qualities by the formulation of granules of desired hardness and size. Suitable binder materials include, but are not limited to, starch (including corn starch and pregelatinzed starch), gelatin, sugars (including sucrose, glucose, dextrose, lactose and sorbitol), polyethylene glycol, waxes, natural and synthetic gums, e.g., acacia, tragacanth, sodium alginate, celluloses, and Veegum, and synthetic polymers such as polymethacrylates and polyvinylpyrrolidone.

Lubricants have a number of functions in tablet manufacture. They prevent adhesion of the tablet material to the surface of the dies and punches, reduce interparticle friction, facilitate the ejection of the tablets from the die cavity and may improve the rate of flow of the tablet granulation. Examples of suitable lubricants include, but are not limited to, magnesium stearate, calcium stearate, stearic acid, glyceryl behenate, talc, sodium lauryl sulfate, sodium stearyl fumarate, polyethylene glycol or mixtures thereof. Generally, the lubricant is present in an amount from about 0.25% to about 5% of the weight of the final composition and more specifically from about 0.5 to about 1.5% of the weight of the final composition.

A disintegrant is a substance, or a mixture of substances, added to a tablet to facilitate its breakup or disintegration after administration. Materials serving as disintegrants have been classified chemically as starches, clay, celluloses, aligns, gums and cross-linked polymers. Examples of suitable disintegrants include, but are not limited to, crosscarmelose sodium, sodium starch glycolate, starch, magnesium aluminum silicate, colloidal silicon dioxide, methylcellulose, agar, bentonite, alginic acid, guar gum, citrus pulp, carboxymethyl cellulose, microcrystalline cellulose, or mixtures thereof. Generally, the disintegrant is present in an amount from about 0.5% to about 25% of the weight of the final composition and more specifically from about 1% to about 15% of the weight of the final composition.

Glidants are substances which improve the flow characteristics of a powder mixture. Examples of glidants include, but are not limited to colloidal silicon dioxide, talc or mixtures thereof. Generally, the glident is present in an amount of from about 0.1% to about 10% of the weight of the final composition and more specifically from 5 about 0.1% to about 5% of the weight of the final composition.

The adsorbent may be, for example colloidal silicon dioxide, microcrystalline cellulose, calcium silicate or mixtures thereof. Generally, the adsorbent is present in an amount from about 0.05% to about 42% of the weight of the final composition and more specifically from about 0.05% to about 37% of the weight of the final composition.

If desired, other ingredients, such as diluents, stabilizers and anti-adherents, conventionally used for pharmaceutical formulations may be included in the present formulations. Optional ingredients include coloring and flavoring agents which are well known in the art.

The pharmaceutical composition described in the present invention may be formulated to release the active ingredients in a sustained release manner. Various formulations, including elixers, suspensions, tablets, caplets, capsules, and the like are contemplated for dosage forms of these components.

The invention is further described by means of the following examples, which are not intended to limit the scope of the claimed invention in any manner.

EXAMPLE 1

Pharmaceutical compositions dosage forms of the present invention are made of the active ingredients listed below in the following dosage amounts.

TABLE 1

| NSAID | Decongestant | Antihistamine |
|---|---|---|
| Ibuprofen 200 mg | Pseudoephedrine 30 mg | Chlorpheniramine 2 mg |
| Ibuprofen 400 mg | Pseudoephedrine 60 mg | Chlorpheniramine 4 mg |
| Ibuprofen 200 mg | Pseudoephedrine 30 mg | Brompheniramine 2 mg |
| Ibuprofen 200 mg | Pseudoephedrine 30 mg | Diphenhydramine HCl 12.5 mg |
| Ibuprofen 200 mg | Phenylpropanolamine HCl 37.5 mg | Clemastine fumarate 0.67 mg |

EXAMPLE 2

A study was run to evaluate and compare the analgesic/decongestant/antihistaminic efficacy of a caplet composition that includes an effective amount of each of ibuprofen, pseudoephedrine HCl and chlorpheniramine maleate, to a combination of the pseudoepedrine and chlorpheniramine in a tablet. The study was a multicenter, outpatient, multiple-dose, placebo controlled, double-blind, double-dummy, parallel-group, randomized trial.

Selection of patients. The study enrolled 1070 appropriately selected patients who were at least 12 years of age and included both males and females. Study participants were required to have: (1) at least a two year history of seasonal allergic rhinitis (which encompassed one or more of the following symptoms runny nose, itchy/watery/red eyes, nasal congestion, sneezing, itchy nose/throat/palate, allergy associated headache and facial pain/pressure/discomfort) and (2) a history of experiencing at least moderate headache, and/or facial pain/pressure/discomfort which worsened during the allergy season and responded to over-the-counter (OTC) analgesics (based upon self report). Qualified subjects were required to undergo a 3-30 day run-in phase to establish that the patients had sufficiently severe allergy symptoms, during which time they reflectively assessed the severity of the following symptoms in the morning (upon waking) and in the evening (prior to bedtime): nasal congestion, sneezing, rhinorrhea, itchy nose/throat/palate; itchy/watery/red eyes and headache/facial pain/pressure/discomfort. The severity of each symptom was assessed using a 4-point categorical scale where 0=none (no symptom present), 1=mild (minimal awareness of symptom, symptom easily tolerated), 2=moderate (symptom present and bothersome, but tolerable) and 3=severe (symptom hard to tolerate; may cause interference with daily activities/sleeping). They were also asked if the pain was a headache or facial pain/pressure/discomfort and were also asked to rank the pain from 0=none (no symptom present), 1=mild (minimal awareness of symptom, symptom easily tolerated), 2=moderate (symptom present and bothersome, but tolerable) and 3=severe (symptom hard to tolerate; may cause interference with daily activities/sleeping). Patients were administered the first dose of study medication (Day 1) when the patient experienced allergy-associated pain of at least moderate intensity and had a summed reflective allergy symptom score of at least 48 for the previous six morning and evening assessments of symptom severity. Patients were also assessed for allergy associated pain and were asked if they were in pain.

Of the 1070 subjects enrolled in the study and included in the safety analysis, 1044 qualified for the intent-to treat analysis and of these 1044 patients, 256 received Treatment 1; 265 received Treatment 2; 266 received Treatment 3; and 257 received Treatment 4. See below for a description of the treatments. Additionally 1032 patients were included in the modified intent to treat analysis.

Dosage composition. The patents in the study were randomly placed into four treatment groups. Treatment 1 consisted of one placebo tablet plus 2 ibuprofen/pseudoephedrine/chlorpheniramine (200/30/2 mg per caplet respectively) caplets for a total dose of 400/60/4 mg of ibuprofen/pseudoephedrine/chlorpheniramine every 6 hours. Treatment 2 consisted of one placebo tablet, one placebo caplet plus one ibuprofen/pseudoephedrine/chlorpheniramine (200/30/2 mg per caplet respectively) caplet every 6 hours. Treatment 3 consisted of one tablet of pseudoephedrine/chlorpheniramine (30/2 mg per tablet respectively) plus 2 placebo caplets every 6 hours. Treatment 4 consisted of 1 placebo tablet and two placebo caplets every 6 hours.

Dosage timing and monitoring of symptoms. The patients were dosed approximately every 6 hours 3 times per day (morning, midday and evening) up to a total of 19-21 doses over 7 days. Two and three hours after taking the first dose, the patients assessed the severity of their allergy-associated pain on a 4 point scale 0=none (no symptom present), 1=mild (minimal awareness of symptom, symptom easily tolerated), 2=moderate (symptom present and bothersome, but tolerable) and 3=severe (symptom hard to tolerate; may cause interference with daily activities/sleeping). Prior to each subsequent dose the patients indicated whether or not they were experiencing any allergy-associated headache and/or facial pain/pressure/discomfort (yes or no answer required). On the evening of Day 1 (prior to bedtime) and on each morning (upon awakening) and evenings of Days 2-7 the patients self-assessed the severity of the following allergy symptoms: nasal congestion, sneezing, rhinorrhea, itchy nose/throat/palate, itchy/watery/red eyes, and allergy associated headache and/or facial pain/pressure/discomfort. The severity of each symptom was assessed using a 4-point categorical scale where 0=none (no symptom present), 1=mild (minimal awareness of symptom, symptom easily tolerated), 2=moderate (symptom present and bothersome, but tolerable) and 3=severe (symptom hard to tolerate; may cause interference with daily activities/sleeping). On the evening of Day 7, after completing the allergy symptom assessment, subjects provided an overall assessment of the study medication, ranking the treatment for allergy symptoms on a scale of 0 (poor) to 4 (excellent). In addition, the patients evaluated any adverse experiences they experiences they experienced during the 7 day study medication period. The patients evaluated the adverse experience as either mild, moderate or severe. Examples of adverse experiences include, but are not limited to, somnolence, dry mouth, dizziness, and insomnia.

Criteria for evaluation. The primary efficacy parameter was the amount of change from the baseline in the 7 day, overall average reflective total symptoms score. Secondary Efficacy Parameters included key variables: (1) the time weighted sun of the pain intensity difference scores at two and three hours after the first dose of the study; (2) the change from the baseline in the overall average reflective total antihistamine symptoms score (sneezing, itchy/watery/red eyes, itchy nose/throat/palate) minus the overall average reflective total symptoms score; (3) the incidence of pre-dosing allergy associated pain (excluding the baseline measurement); (4) the change from the baseline in the average total reflective symptom score for each treatment day; (5) the overall evaluation of the study medication.

Statistical analysis. All analyses were performed using SAS® Version 6.12. Onset of symptom relief was defined as the first time point where a subject experienced a $\geq 15\%$ reduction from baseline in the total symptom score. If a subject did not experience a $\geq 15\%$ reduction from baseline during the entire course of the study, time to onset was censored and assigned a score of 7 days. Statistically significant treatment differences were declared if the probability of a random occurrence between the treatment groups was $\leq 0.05$. Statistical trends were declared if the probability of random occurrence between treatment groups was $0.05 < p \leq 0.15$ or the observed difference between treatment groups was at least 10%. Other appropriate statistical measures were employed as appropriate and as within the skill in the art to validate the study.

All variables based upon changes from baseline were analyzed via an ANOVA model including for effects of treatment, corresponding baseline and center. In addition, treatment-by-baseline and treatment-by-center interaction effects were assessed. The incidence of pre-dose allergy-associated pain (excluding baseline) was analyzed via a repeated measures logistics model. The model was fitted via generalized estimating equations with exchangeable correlation structure. Effects for treatment and baseline pain severity were included in the model. The overall evaluation of study medication scores was analyzed by the Cochran-Mantel-Haenszel test, controlling for center, using modified ridit scores. In addition, the treatment-by-center interaction was computed using the pseudo-homogeneity test. The distribution of time to onset of symptom relief was estimated using Kaplan-Meier estimates; the median time and their 95% confidence limits were derived by the method of Simon and Lee.

For each parameter analyzed via the ANOVA model, the 955 confidence interval for treatment differences was derived based upon on the differences in the least squares means and the corresponding standard error. The 95% confidence interval for each pair wise treatment difference in the incidence of allergy associated pain and the time to onset of symptom relief were based on the log-odds ratio and log hazard ratio, and their corresponding standard errors, respectively (based upon Wald's test). The confidence interval for treatment differences in the overall evaluation of the study medication was based on the Goodman-Kruskal Gamma statistic and its standard error.

Efficacy Results. A total of 1044 patients were enrolled and took at least one dose study of medication. A total of 957 patients completed the study. A total of 1044 patients were included in the analysis of all efficacy variables, save for the time-weighted sum of the pain intensity difference, where 1032 patients were evaluated.

In the analysis of efficacy variables, the interaction effects of treatment-by-baseline and treatment-by-site were found to be generally not significant (p>0.1) across variables. The baseline means for individual reflective symptoms were nasal congestion 2.3, sneezing 1.7, runny nose 2.0, itchy nose/throat/palate 2.0, itchy/watery/red eyes 2.0 and headache/facial pain/pressure/discomfort 2.3, respectively. The mean reflexive symptom score and the mean total reflexive antihistamine score at baseline were 12.21 and 5.71, respectively. The allergy-associated pain when the first dose of the study medication was given to the patients was rated moderate by 49% and severe by 51% of the subjects among the 1032 patients who where evaluated for the time weighted sun of the pain intensity difference. Almost all of the subjects (99.6%) were experiencing allergy associated pain at the time the first dose of study medication was taken. The treatment groups were comparable with respect to the above baseline variables as well as the baseline individual reflective symptoms.

The results of the primary efficacy parameter and key secondary parameters highlighted that the Treatment 1 and Treatment 2 (lower dosages) resulted in significantly better results than Treatment 3 (no ibuprofen) and Treatment 4 (full placebo).

The time-weighted sums of the pain intensity differences over 3 hours for the patients were 2.8 for the Treatment 1 and Treatment 2 groups. Treatment 3 and Treatment 4 had scores of 2.1 and 2.0, respectively. The mean change from baseline in the overall average reflective total symptom score for Treatments 1-4 were 5.6, 5.4, 4.6, and 3.8, respectively. The mean changes from baseline in the overall overage total reflective antihistamine symptoms score for Treatment groups were 2.9, 2.8, 2.4 and 1.9, respectively.

Thus the patients in the Treatment 2 group experienced a 33% improvement in the time-weighted sum of the pain intensity differences over 3 hours and a 17% improvement in the mean change from baseline in the overall average reflective total symptom score over the Treatment 3 group (no ibuprofen). The patients in Treatment 2 group also experienced a 47% improvement in the mean change from baseline in the overall overage total reflective antihistamine symptoms score over the Treatment 4 group. While the patients in Treatment 1 group exhibited numerically better composite scores for all of the allergy symptoms and histamine mediated symptoms, a statistical trend could not be established. In addition Treatment 1 and Treatment 2 groups had almost the same scores for the time-weighted sum of the pain intensity differences.

The results show that the 2 mg dose of chlorpheniramine is effective as an antihistamine, for it is more effective than the placebo in alleviating histamine-mediated symptoms. Also patients in Treatment group 1 identified an increase in somnolence as compared to Treatment group 2.

Conclusions. The results of the study demonstrate that there is significant analgesic/decongestant/antihistaminic efficacy of ibuprofen/peudoephedrine/chlorpheniramine at the given dosages in the treatment of the tested symptoms relative to decongestant and antihistamine alone. It was surprisingly found that ibuprofen contributes to the overall effectiveness of the combination by not only relieving allergy-associated pain but by also reducing the severity of other seasonal allergic rhinitis symptoms. This is shown by the overall greater effectiveness of Treatment 2 (which contains ibuprofen) compared to Treatment 3 (which did not contain ibuprofen). It also was surprisingly found that both dosages of ibuprofen/pseudoephedrine/chlorpheniramine (400/60/4 and 200/30/2 mg total, respectively) were equally efficacious in relieving histamine-mediated symptoms of seasonal allergic rhinitis. In addition, a clear dose response was not seen between the Treatment 1 and Treatment 2 groups.

All treatments were tolerated and the incidence of adverse experiences were consistent with those reported for similar medications containing the same doses of pseudoephedrine and chlorpheniramine. The proposed dose of ibuprofen/pseudoephedrine/chlorpheniramine is 1-caplet every four to six hours—not to exceed 6 caplets in a 24-hour period—since both doses of I/P/C were equally effective and the 2-caplet I/P/C dose demonstrated an increased incidence of somnolence, dry mouth and asthenia relative to the 1-caplet dose. This dosing will allow for the product to be taken prior to bedtime and/or during the night (in addition to daytime dosing) and is consistent with the approved OTC daily dose of ibuprofen (1200 mg), and is still below the monograph daily doses of pseudoephedrine (240 mg) and chlorpheniramine (24 mg).

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

All patents, applications, articles, publications, and test methods mentioned above are hereby incorporated by reference.

What is claimed is:

1. A unit dosage form comprising about 18 to about 33 mg pseudoephedrine, about 1.2 to about 2.2 mg chlorpheniramine, and about 100 to about 200 mg ibuprofen per said unit dosage form.

2. The unit dosage form of claim 1 in the form of a tablet, trochet, dispersion, suspension, solution, elixir, capsule or patch.

3. The unit dosage form of claim 1 further comprising at least one excipient selected from the group consisting of lubricants, disintegrants, glidents, adsorbents, and mixtures thereof.

4. The unit dosage form of claim 1 comprising about 21 to about 30 mg pseudoephedrine, about 1.4 to about 2.0 mg chlorpheniramine, and about 100 to about 200 mg ibuprofen per said unit dosage form.

5. The unit dosage form of claim 4 in the form of a tablet, trochet, dispersion, suspension, solution, elixir, capsule or patch.

6. The unit dosage form of claim 4 further comprising at least one excipient selected from the group consisting of lubricants, disintegrants, glidents, adsorbents, and mixtures thereof.

7. The unit dosage form of claim 4 comprising about 30 mg pseudoephedrine, about 2.0 mg chlorpheniramine, and about 200 mg ibuprofen per said unit dosage form.

8. The unit dosage form of claim 7 in the form of a tablet, trochet, dispersion, suspension, solution, elixir, capsule or patch.

9. The unit dosage form of claim 7 further comprising at least one excipient selected from the group consisting of lubricants, disintegrants, glidents, adsorbents, and mixtures thereof.

* * * * *